(12) United States Patent
Koch

(10) Patent No.: US 8,182,144 B2
(45) Date of Patent: May 22, 2012

(54) TEMPERATURE-MEASURING DEVICE FOR A RESPIRATION HUMIDIFIER

(75) Inventor: Jochim Koch, Ratzeburg (DE)

(73) Assignee: Dräger Medical GmbH, Lübeck (DE)

( * ) Notice: Subject to any disclaimer, the term of this patent is extended or adjusted under 35 U.S.C. 154(b) by 961 days.

(21) Appl. No.: 12/167,426

(22) Filed: Jul. 3, 2008

(65) Prior Publication Data

US 2009/0041080 A1  Feb. 12, 2009

(30) Foreign Application Priority Data

Aug. 11, 2007  (DE) .......................... 10 2007 037 955

(51) Int. Cl.
*G01K 1/14* (2006.01)
(52) U.S. Cl. ........................................ 374/147; 374/141
(58) Field of Classification Search .................. 374/120, 374/121, 123, 135, 138, 141, 147, 148
See application file for complete search history.

(56) References Cited

U.S. PATENT DOCUMENTS

| | | | | |
|---|---|---|---|---|
| 4,121,763 A * | 10/1978 | Roberge | .......................... | 374/147 |
| 5,163,423 A | 11/1992 | Suzuki | | |
| 5,326,171 A * | 7/1994 | Thompson et al. | ............ | 374/121 |
| 5,355,845 A * | 10/1994 | Burgess et al. | ................ | 374/121 |
| 5,460,041 A * | 10/1995 | Andes et al. | ................... | 374/148 |
| 5,632,556 A * | 5/1997 | Sivyer | ............................ | 374/148 |
| 5,826,982 A | 10/1998 | Schieferdecker et al. | | |
| 5,829,880 A * | 11/1998 | Diedrich | ........................ | 374/147 |
| 6,390,668 B1 | 5/2002 | Materna | | |
| 7,080,940 B2 * | 7/2006 | Gotthold et al. | .............. | 374/121 |
| 2008/0205481 A1 * | 8/2008 | Faries et al. | .................... | 374/148 |
| 2010/0170483 A1 * | 7/2010 | Wienand et al. | .............. | 374/148 |
| 2011/0038394 A1 * | 2/2011 | Ma et al. | ........................ | 374/148 |

FOREIGN PATENT DOCUMENTS

WO  WO 2004/020031 A1  3/2004

\* cited by examiner

*Primary Examiner* — G. Bradley Bennett
(74) *Attorney, Agent, or Firm* — McGlew and Tuttle, P.C.

(57) ABSTRACT

A contactless temperature-measuring device especially for a respiration humidifier with a flow channel for breathing gas, which is improved in respect to handling and reliability of measurement. The device includes: a hollow body (1), which is closed towards the flow channel (2, 6), extends into the flow channel (2, 6) for assuming the temperature in the flow channel (2, 6); and an infrared detector (3, 7) is directed toward the inner surface of the hollow body (1) extending into the flow channel (2, 6) for the contactless detection of the temperature of the hollow body (1).

20 Claims, 8 Drawing Sheets

TEMPERATURE-MEASURING DEVICE FOR A RESPIRATION HUMIDIFIER

CROSS REFERENCE TO RELATED APPLICATIONS

This application claims the benefit of priority under 35 U.S.C. §119 of German Patent Application DE 10 2007 037 955.4 filed Aug. 11, 2007, the entire contents of which are incorporated herein by reference.

FIELD OF THE INVENTION

The present invention pertains to a temperature-measuring device for a respiration humidifier.

BACKGROUND OF THE INVENTION

The breathing gas temperature at the outlet of the mixing chamber with the humidified breathing gas is measured in prior-art respiration humidifiers by means of a temperature-dependent resistor element, and the heat output of the water reservoir is regulated accordingly. In disposable flexible breathing tube systems, a reusable temperature sensor, which is connected by a cable to the humidifier proper having a heating means, is plugged for this purpose into the flexible tube. To avoid cross infections, this reusable temperature sensor must be cleaned and sterilized or disinfected after use. There remains a hygienic risk if the procedure is not carried out carefully. The temperature sensor must be sufficiently sealed in the flexible tube system to prevent leaks from developing. The handling of this prior-art design or system is complicated. As an alternative, the temperature sensor may be integrated in the flexible breathing tube system as a fixed component of this system, which leads to higher costs in case of disposable flexible tube systems if the temperature sensor is disposed of together with the flexible tube system after use. Cables must be additionally led from the respiration humidifier to the flexible tube system in case of flexible tube systems used several times, which may lead to additional costs, and due to the repeated cleaning, disinfection or sterilization operations, to limited reliability of operation of the cables and electric plug connections.

SUMMARY OF THE INVENTION

The object of the present invention is to propose a temperature-measuring device especially for a respiration humidifier, which is improved in respect to the handling and reliability of the measurement and can be used for both disposable and reusable systems.

According to one embodiment, a temperature-measuring device for a respiration humidifier may be provided with at least one flow channel for a breathing gas. The device may comprise a hollow body having a closed end surface. The hollow body may extend into the at least one flow channel for assuming a temperature in the at least one flow channel. The hollow body may have an inner surface. An infrared detector may face in a direction of the inner surface of the hollow body for the contactless detection of the temperature of the hollow body. An essential advantage of the contactless temperature-measuring means being proposed for respiration humidifiers consists of the physical uncoupling of the temperature sensor system proper from the temperature measurement site, so that the drawbacks experienced hitherto in the case of the prior-art solutions are eliminated.

The hollow body may be substantially cylindrical or may be in a form of a cone or a truncated cone having a base arranged in the flow channel.

The hollow body may have an emission coefficient of about 1.0 for heat radiation.

One hollow body may be located on a first flow channel leading out of a mixing chamber of the respiration humidifier and/or another hollow body may be located on a second flow channel leading into the mixing chamber of the respiration humidifier. One infrared detector may be arranged adjacent to the first flow channel. Another infrared detector may be arranged adjacent to the second flow channel.

The infrared detector may comprise a plurality of infrared measuring elements in the form of a thermopile.

The infrared detector may comprise a band pass filter. The band pass filter filters external radiation from the environment such that the external radiation from the environment at the site of measurement is minimized in the infrared detector.

The infrared detector may comprise an optical component. The optical component focuses an angle of vision of the infrared detector to the hollow body.

The hollow body and the at least one flow channel may form an assembly unit.

The respiration humidifier may be connected to a respirator or anesthesia apparatus.

The at least one flow channel may comprise a Y-piece structure.

The at least one flow channel may comprise a flexible tube composed of a plastic ranging from opal to transparent.

The temperature-measuring device may comprise a control means for controlling heat output of the respiration humidifier based on temperatures detected by the infrared detectors.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
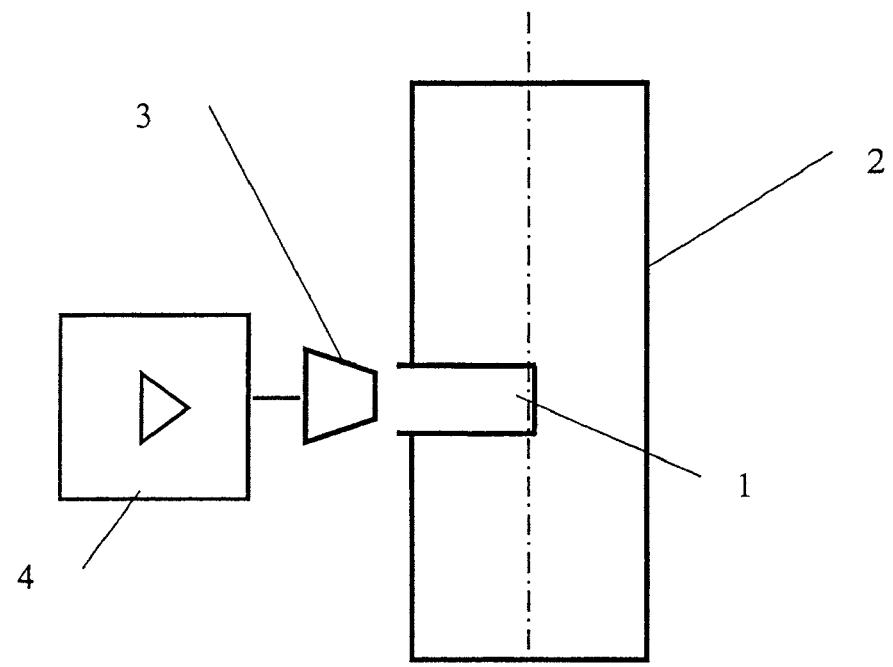
FIG. 1 is a schematic view of a basic arrangement of the temperature-measuring device for a respiration humidifier.

Referring to the drawings in particular, FIG. 1, a flow channel 2 leading out of, for example, a respiration humidifier, is provided with a hollow body 1, which extends or protrudes into the central longitudinal axis of the flow channel 2 and is especially cylindrical.

The hollow body 1 is used to assume the temperature of the breathing gases flowing in the flow channel 2. The temperature in the hollow body 1 and thus the corresponding temperature of the breathing gas flow is detected with the correspondingly oriented infrared detector 3 from the outside and in a physically uncoupled manner.

The surface of the material of the hollow body 1 is selected to be such that the emission coefficient for heat radiation is as close to 1.0 as possible. As an alternative, the surface of the hollow body 1 is blackened.

The hollow body 1 assumes an average temperature during the measurement. The heat dissipation to the environment or to the flow channel 2 is minimized via the especially thin walls of the hollow body.

Figure 4:
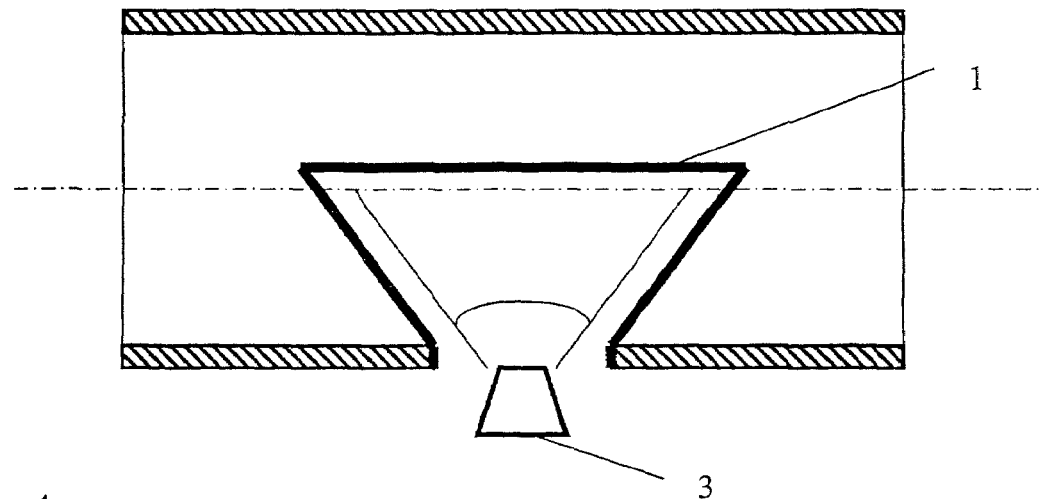
FIG. 4 is a cross sectional view of an embodiment of the hollow body of a truncated cone shape with a focused angle of vision of the infrared detector to the base of the hollow body.
Figure 5:
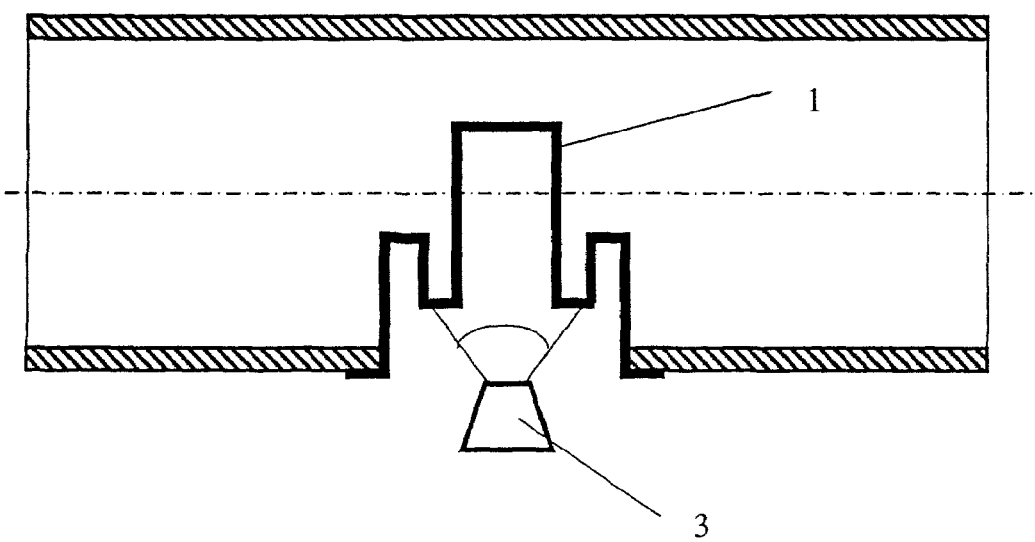
FIG. 5 is a cross sectional view of an embodiment of the hollow body in a meandering shape with a focused angle of vision of the infrared detector to the central area of the hollow body.

Distortion of the temperature measurement by heat dissipation from the hollow body 1 to the usually cooler wall of the flow channel 2 can be additionally reduced or practically eliminated by a special shape of the hollow body 1 (FIGS. 4 and 5), by focusing the angle of vision of the infrared detector 3 by means of an optical component and/or optionally by heat insulation between the hollow body 1 and the flow channel 2.

It is especially advantageous that contrary to the prior-art configurations, no cable connections, which would lead to a considerable heat conduction and distortion of the measured temperature, are necessary from the flow channel 2.

The weight of the hollow body 1 is very low, so that it has a low thermal inertia and thus makes possible a rapid and dynamic temperature measurement.

The hollow body 1 can be manufactured at a very low cost and with precise geometry, especially according to the plastic injection molding technique, so that it can be pressed into the flow channel 2 from the outside or from the inside and can be reliably sealed.

As an alternative, the hollow body 1 is an integral part of the flow channel 2 or is made in one piece therewith.

The hollow body 1 is preferably designed in the form of a cylinder or of a cone or of a truncated cone, and the base is located inside the flow channel 2.

The infrared detector 3 is uncoupled from the hollow body 1, and the temperature measurement is carried out in a contactless manner. The infrared detector 3 is preferably positioned in the respiration humidifier such that when the flow channel 2 with a mixing chamber 5 (FIG. 2) belonging to it is replaced, the infrared detector automatically detects the inner surface or the temperature of the hollow body 1.

The analysis of the measured value for the control of the heating temperature of the respiration humidifier is carried out by means of an analyzing unit 4 connected to the infrared detector 3.

Figure 2:
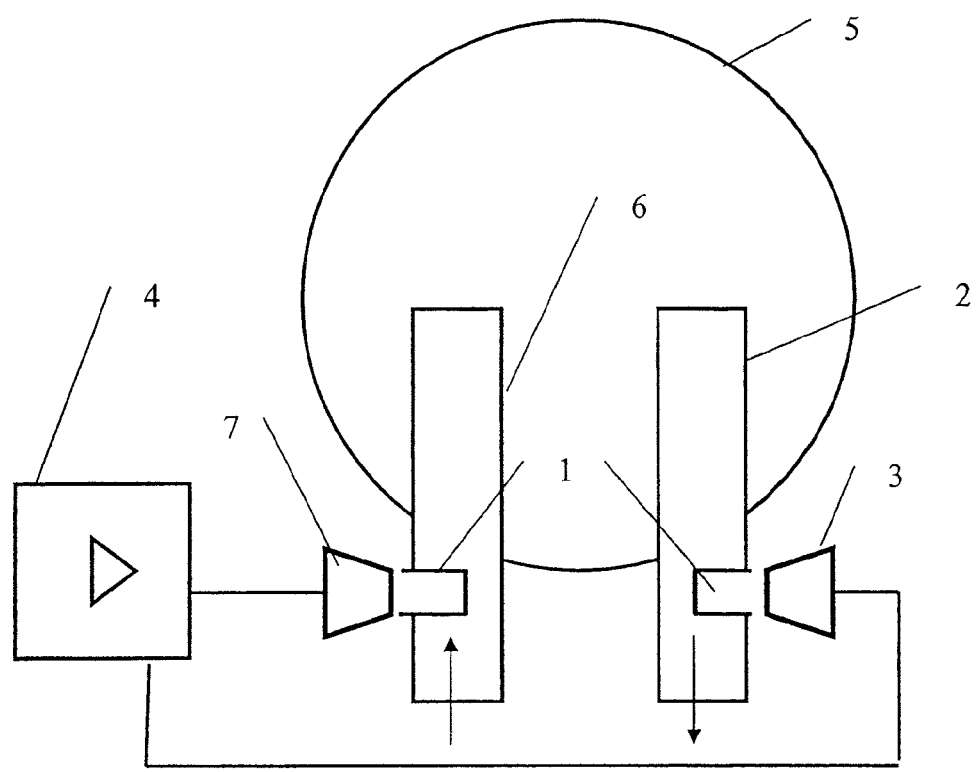
FIG. 2 is a schematic view of an arrangement of two temperature-measuring device in a respiration humidifier.
Figure 3:
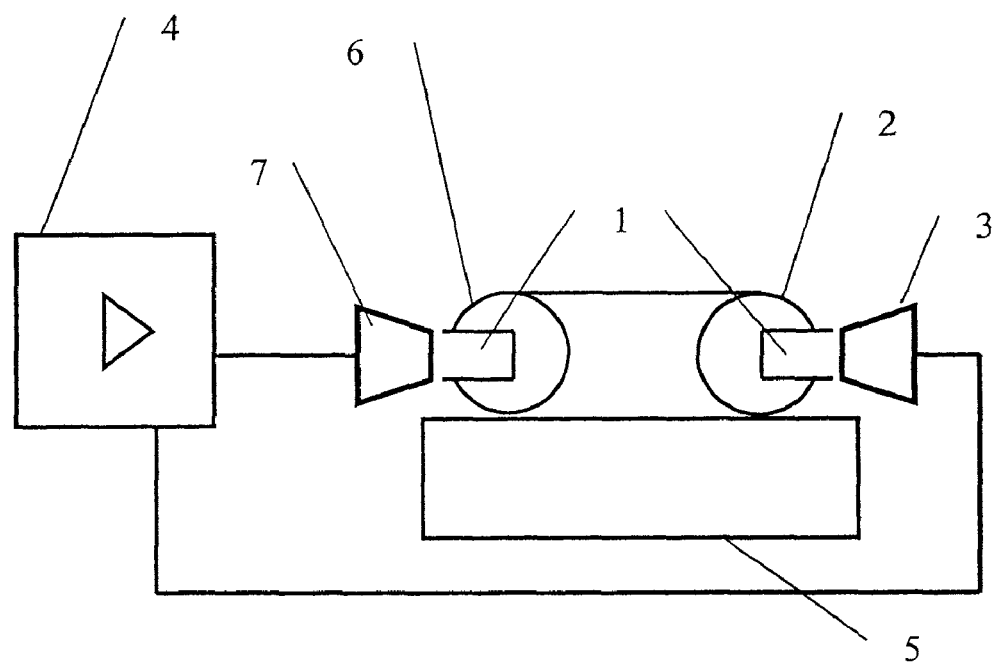
FIG. 3 is a vertical section view of through the temperature-measuring device of FIG. 2.

According to FIG. 2, the respective input and output temperatures of the breathing gas are measured in both the flow channel 2 leading out of the mixing chamber 5 of the respiration humidifier and the flow channel 6 leading into the mixing chamber 5, so that it is possible to control the heat output of the respiration humidifier as a function of both temperatures by means of the analyzing unit 4. The flow channel 6 sends the breathing air or the breathing gas into the mixing chamber 5. The humidified breathing gas is sent from the mixing chamber 5 to a patient being respirated, not shown, via the flow channel 2.

The infrared detectors 3, 7 preferably comprise a plurality of infrared measuring elements each in the form of a thermopile with a measuring precision of, e.g., 0.2 K in a temperature range of 20° C. to 40° C.

This is completely sufficient for practical use in a respiration humidifier.

The infrared detectors 3, 7 used are preferably equipped with an infrared filter in order for the surface temperature of the hollow body 1 to be able to be detected specifically in a narrow infrared wavelength range.

The angle of vision of the infrared detector 3 is specifically limited to the hollow body 1 by means of an optical system.

The infrared detector 3 or 7 is optionally pressed mechanically onto the hollow body 1 by means of a spring element in order to minimize or eliminate external radiation, which could become disturbingly noticeable through the gap between the infrared detector 3, 7 and the hollow body 1. A band pass filter can be used to avoid possible disturbances in the temperature measurement due to the humidity of the ambient air.

The infrared detector 3, 7 is calibrated once before the measurement, for example, by balancing with a black body of a certain temperature, and it can then be used over rather long periods of time.

The hitherto necessary handling of the temperature sensors is eliminated by the present uncoupled temperature-measuring device for a respiration humidifier. Cleaning or disinfection of the infrared detectors 3, 7 is not necessary because there is no contact with surfaces carrying breathing gas.

Very good measurement dynamics with minimized environmental effects is possible due to the minimum heat flux of the hollow body 1 and the absence of cables.

The arrangement is electrically intrinsically safe due to the absence of electric contacts and connections to the breathing gas flow.

The costs for consumable parts are markedly reduced due to the measuring sensor system being arranged outside the flexible tube system/humidifying chamber.

Figure 6:
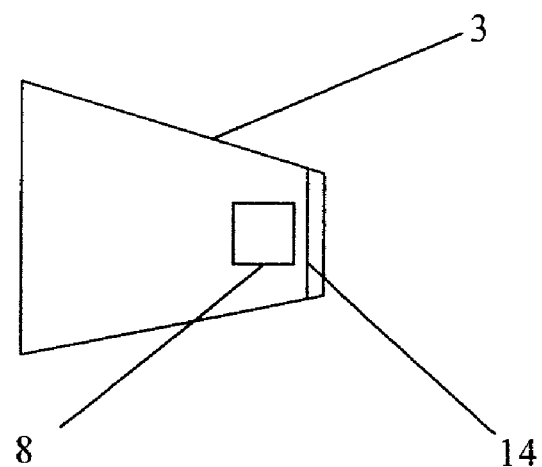
FIG. 6 is a side view of the infrared detector.

FIG. 6 shows the infrared detector 3 having an optical component 8. The optical component 8 focuses the angle of vision of the infrared detector 3 toward the hollow body 1. The infrared detector 3 is equipped with a band pass filter 14 so that external radiation from the environment is minimized in the infrared detector.

Figure 7:
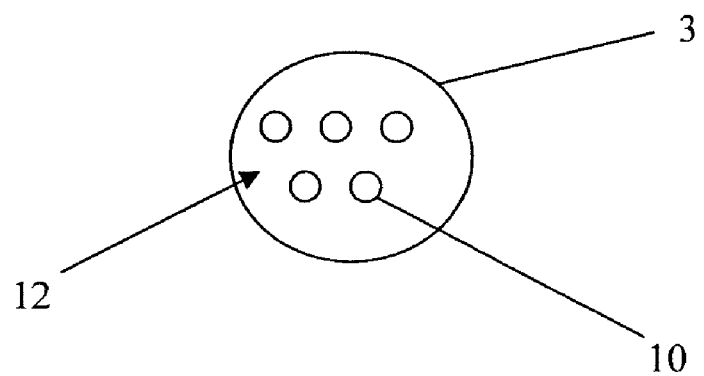
FIG. 7 is a front view of the infrared detector of FIG. 6.

FIG. 7 shows the infrared detector 3 with a plurality of infrared measuring elements 10 that are in the form of a thermopile 12

Figure 8:
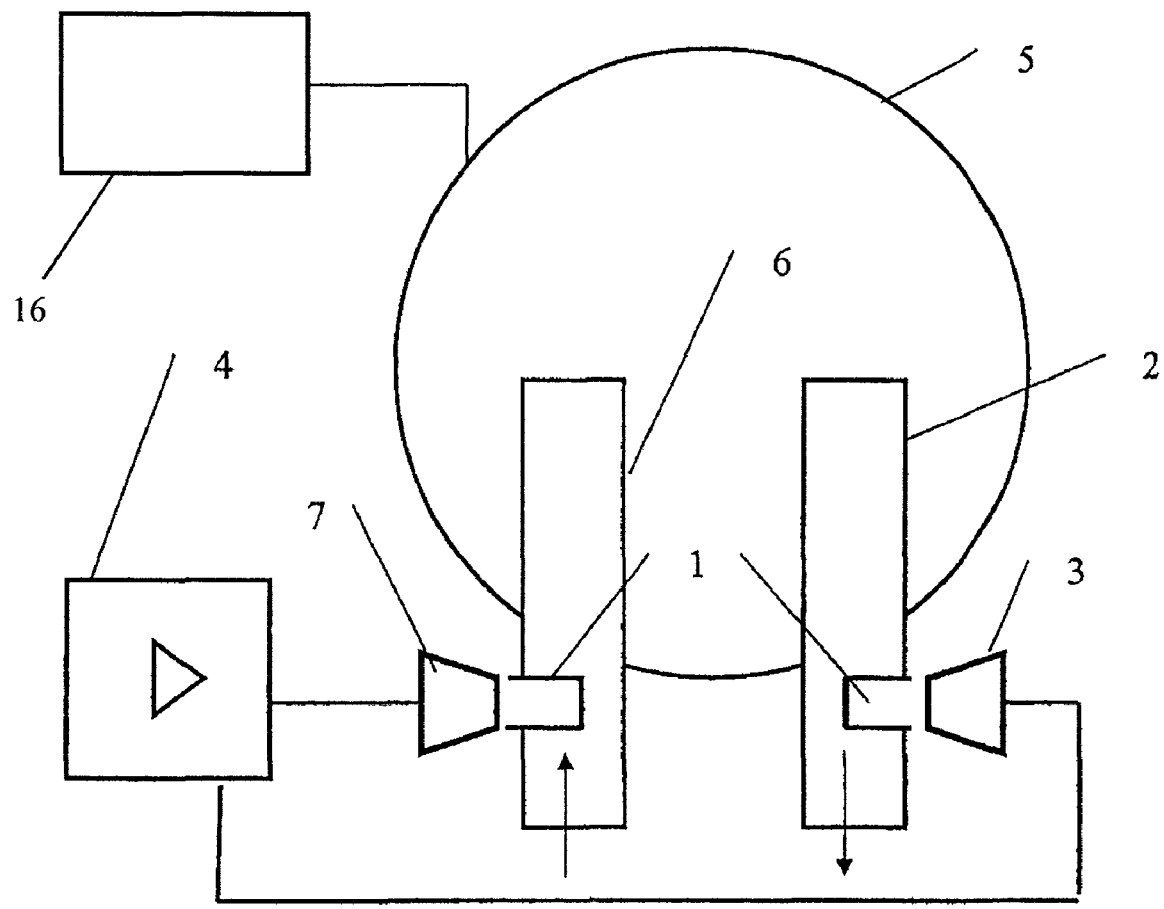
FIG. 8 is another schematic view of an arrangement of two temperature-measuring device in a respiration humidifier.

FIG. 8 is a schematic view of the arrangement of an arrangement of two temperature-measuring devices in a respiration humidifier. The respiration humidifier is connected to a respirator 16.

Figure 9:
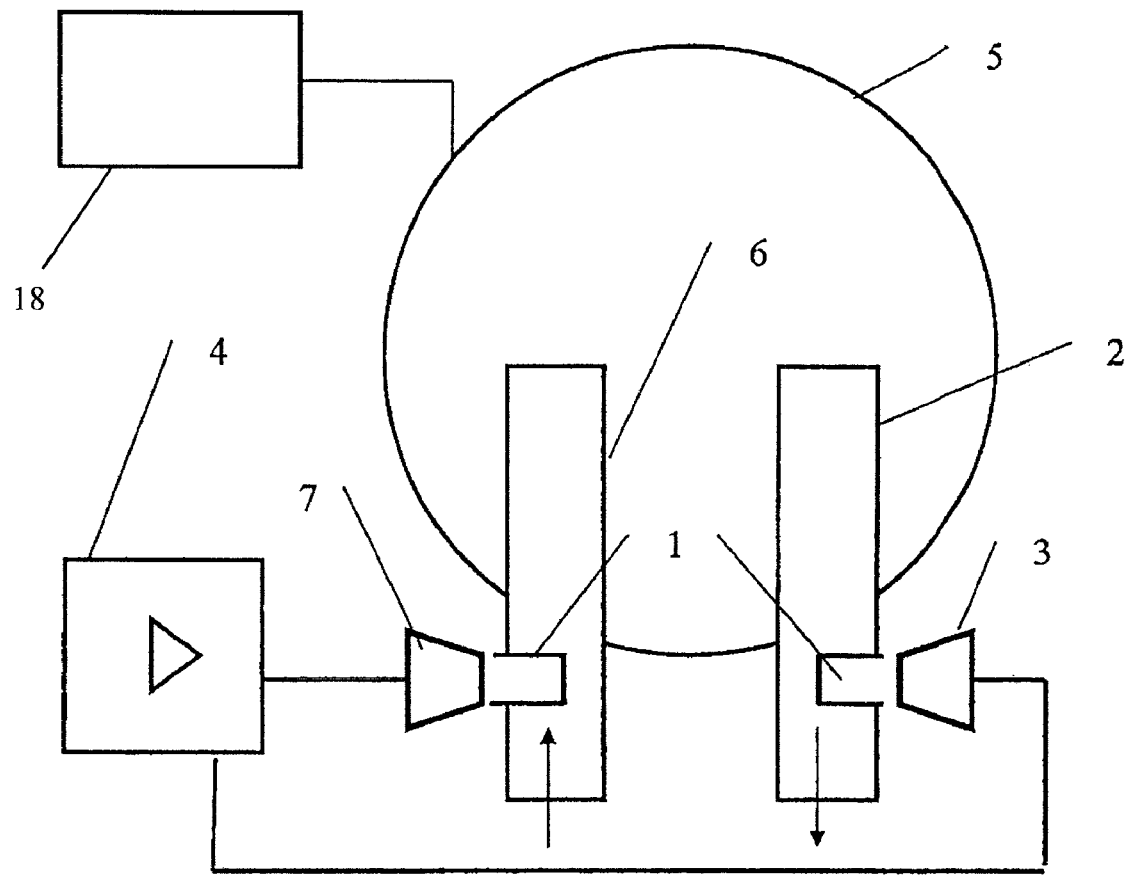
FIG. 9 is yet another schematic view of an arrangement of two temperature-measuring device in a respiration humidifier.

FIG. 9 is a schematic view of the arrangement of an arrangement of two temperature-measuring devices in a respiration humidifier. The respiration humidifier is connected to an anesthesia apparatus 18.

Figure 10:
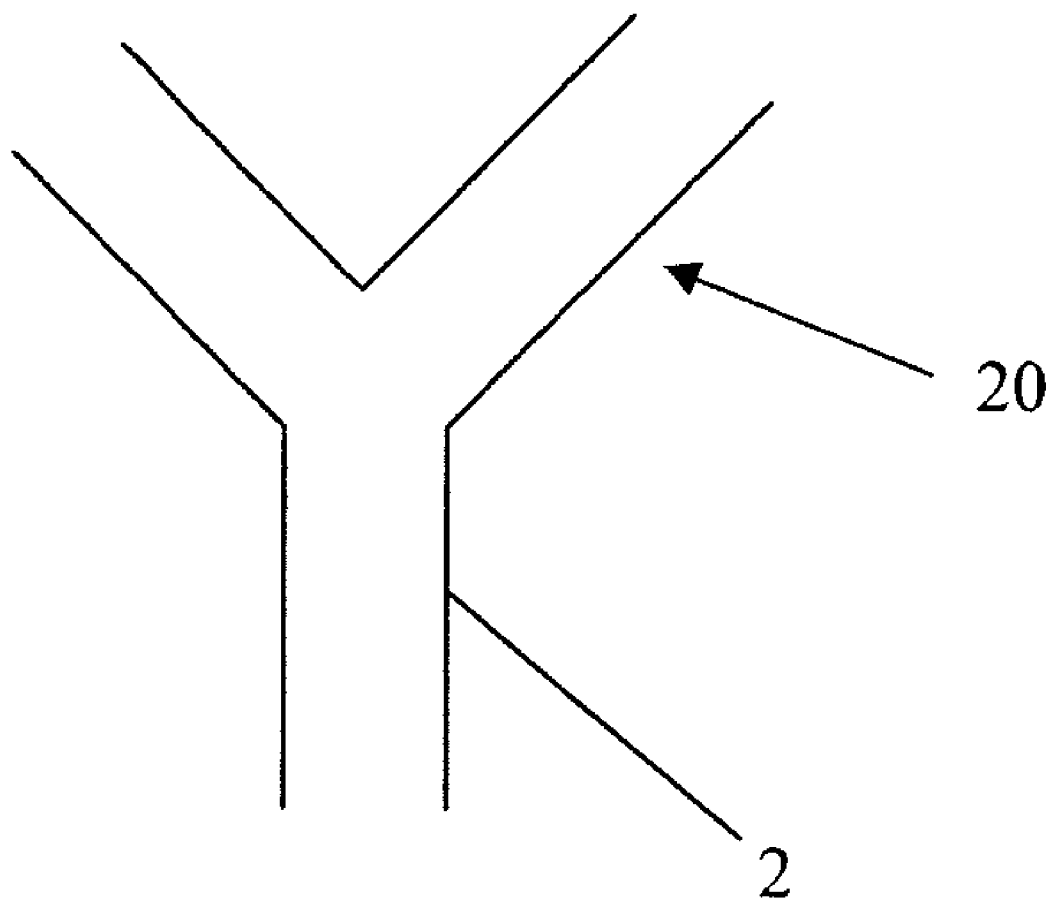
FIG. 10 is a schematic view of a flow channel of the present invention.

FIG. 10 is a schematic view of a flow channel 2 that includes a Y-piece structure 20.

While specific embodiments of the invention have been shown and described in detail to illustrate the application of the principles of the invention, it will be understood that the invention may be embodied otherwise without departing from such principles.

What is claimed is:

1. A temperature-measuring device for a respiration humidifier with at least one flow channel for a breathing gas, the device comprising:
a hollow body having a closed end surface, said hollow body extending into the at least one flow channel for assuming a temperature in the at least one flow channel, said hollow body having an inner surface, said hollow body being located on a first flow channel leading out of a mixing chamber of the respiration humidifier; and
an infrared detector facing in a direction of said inner surface of said hollow body for the contactless detection of the temperature of said hollow body, said infrared detector being arranged adjacent to the first flow channel.

2. A temperature-measuring device in accordance with claim 1, wherein said hollow body is substantially cylindrical or is in a form of a cone or a truncated cone having a base arranged in the flow channel.

3. A temperature-measuring device in accordance with claim 1, wherein said hollow body has an emission coefficient of about 1.0 for heat radiation.

4. A temperature-measuring device in accordance with claim 1, wherein another said hollow body is located on a second flow channel leading into the mixing chamber of the respiration humidifier, another said infrared detector being arranged adjacent to said second flow channel.

5. A temperature-measuring device in accordance with claim 1, wherein said infrared detector comprises a plurality of infrared measuring elements in the form of a thermopile.

6. A temperature-measuring device in accordance with claim 1, wherein said infrared detector comprises a band pass filter, said band pass filter filtering external radiation from the environment such that the external radiation from the environment at the site of measurement is minimized in said infrared detector.

7. A temperature-measuring device in accordance with claim 1, wherein said infrared detector comprises an optical component, said optical component focusing an angle of vision of said infrared detector to said hollow body.

8. A temperature-measuring device in accordance with claim 1, wherein said hollow body and the at least one flow channel form an assembly unit.

9. A temperature-measuring device in accordance with claim 1, wherein the respiration humidifier is connected to a respirator or anesthesia apparatus.

10. A temperature-measuring device in accordance with claim 1, wherein the at least one flow channel comprises a Y-piece structure.

11. A temperature-measuring device in accordance with claim 1, wherein the at least one flow channel comprises a flexible tube composed of a plastic ranging from opal to transparent.

12. A temperature-measuring device in accordance with claim 4, further comprising:
a control means for controlling heat output of the respiration humidifier based on temperatures detected by said infrared detectors.

13. A temperature-measuring device, comprising:
a respiration humidifier with one or more flow channels for receiving a breathing gas;
a hollow body having a hollow body closed end surface, said hollow body extending into said one or more flow channels such that said hollow body has a hollow body temperature equal to a temperature of the breathing gas in said one or more flow channels; and
an infrared detector disposed opposite said hollow body such that said infrared detector detects said hollow body temperature of said hollow body without contacting said hollow body.

14. A temperature-measuring device in accordance with claim 13, wherein said hollow body has an inner surface, said infrared detector facing in a direction of said inner surface of said hollow body.

15. A temperature-measuring device in accordance with claim 13, further comprising:
another hollow body having another hollow body closed end surface, said another hollow body extending into said one or more flow channels such that said another hollow body has another hollow body temperature equal to another temperature of the breathing gas in said one or more flow channels;
another infrared detector disposed opposite said another hollow body such that said another infrared detector detects said another hollow body temperature of said another hollow body without contacting said another hollow body, said one or more flow channels including a first flow channel extending from a mixing chamber of said respiration humidifier and a second flow channel extending into the mixing chamber of said respiration humidifier, said first flow channel receiving humidified breathing gas, said second flow channel delivering non-humidified breathing gas to the mixing chamber of said respiration humidifier, said hollow body being located on said first flow channel, said another hollow body being located on said second flow channel, said infrared detector being arranged adjacent to said hollow body on said first flow channel, said another infrared detector being arranged adjacent to said another hollow body on said second flow channel.

16. A temperature-measuring device in accordance with claim 15, further comprising:
a control unit connected to said infrared detector and said another infrared detector, said control unit controlling heat output of said respiration humidifier based on said hollow body temperature detected by said infrared detector and said another hollow body temperature detected by said another infrared detector.

17. A temperature-measuring device in accordance with claim 16, wherein said hollow body is integrally connected to said first flow channel to form an assembled first flow channel unit, said another hollow body being integrally connected to said second flow channel to form an assembled second flow channel unit.

18. A temperature-measuring device, comprising:
a respiration humidifier with a respiration humidifier housing, said respiration humidifier housing defining a respiration humidifier chamber, said respiration humidifier having a first flow channel and a second flow channel, said first flow channel delivering breathing gas into said respiration humidifier chamber, said second flow channel receiving humidified breathing gas from said respiration humidifier chamber;
a first hollow body having a first hollow body closed end surface, said first hollow body extending into said first flow channel such that said first hollow body has a first hollow body temperature equal to a breathing gas temperature of the breathing gas in said first flow channel;
a first infrared detector disposed opposite said first hollow body such that said first infrared detector detects said first hollow body temperature of said first hollow body without contacting said first hollow body;

a second hollow body having a second hollow body closed end surface, said second hollow body extending into said second flow channel such that said second hollow body has a second hollow body temperature equal to a humidified breathing gas temperature of the humidified breathing gas in said second flow channel;

a second infrared detector disposed opposite said second hollow body such that said second infrared detector detects said second hollow body temperature of said second hollow body without contacting said second hollow body.

19. A temperature-measuring device in accordance with claim 18, further comprising:

a heat output control means connected to said first infrared detector and said second infrared detector for controlling heat output of said respiration humidifier based on said first hollow body temperature and said second hollow body temperature.

20. A temperature-measuring device in accordance with claim 18, wherein said first hollow body is integrally connected to said first flow channel to form an assembled first flow channel unit, said second hollow body being integrally connected to said second flow channel to form an assembled second flow channel unit.

* * * * *